(12) United States Patent
Voges et al.

(10) Patent No.: US 9,062,859 B2
(45) Date of Patent: Jun. 23, 2015

(54) WAFER EDGE INSPECTION ILLUMINATION SYSTEM

(71) Applicant: Rudolph Technologies, Inc., Flanders, NJ (US)

(72) Inventors: Christopher Voges, Eden Prairie, MN (US); Ajay Pai, Crystal, MN (US); Antony Ravi Philip, Apple Valley, MN (US); Tuan D. Le, Porto Alegre (BR)

(73) Assignee: Rudolph Technologies, Inc., Flanders, NJ (US)

( * ) Notice: Subject to any disclaimer, the term of this patent is extended or adjusted under 35 U.S.C. 154(b) by 61 days.

(21) Appl. No.: 13/868,710

(22) Filed: Apr. 23, 2013

(65) Prior Publication Data

US 2014/0063799 A1  Mar. 6, 2014

Related U.S. Application Data

(62) Division of application No. 13/062,852, filed as application No. PCT/US2009/056208 on Sep. 8, 2009, now Pat. No. 8,426,223.

(60) Provisional application No. 61/095,207, filed on Sep. 8, 2008.

(51) Int. Cl.
  *F21V 13/02* (2006.01)
  *G01N 21/95* (2006.01)

(52) U.S. Cl.
  CPC ............ *F21V 13/02* (2013.01); *G01N 21/9503* (2013.01)

(58) Field of Classification Search
  CPC .......................... F21V 13/02; G01N 21/9503
  USPC ........................... 362/235, 231; 382/145, 149
  See application file for complete search history.

(56) References Cited

U.S. PATENT DOCUMENTS

| | | | |
|---|---|---|---|
| 4,618,938 A | 10/1986 | Sandland et al. | |
| 4,644,172 A | 2/1987 | Sandland et al. | |
| 5,592,295 A | 1/1997 | Stanton et al. | |
| 6,194,701 B1 | 2/2001 | Task et al. | |
| 6,215,897 B1 | 4/2001 | Beer et al. | |
| 6,804,385 B2 | 10/2004 | Eisfeld et al. | |
| 6,947,588 B2 * | 9/2005 | Sim | 382/149 |
| 7,084,910 B2 | 8/2006 | Amerson et al. | |
| 7,092,557 B2 | 8/2006 | Eisfeld et al. | |
| 7,149,341 B2 * | 12/2006 | Hayashi et al. | 382/145 |
| 7,170,075 B2 | 1/2007 | Oberski et al. | |
| 7,248,282 B2 | 7/2007 | Maddison | |
| 7,616,804 B2 | 11/2009 | Pai et al. | |
| 7,813,832 B2 | 10/2010 | Sundar | |
| 8,072,503 B2 | 12/2011 | Tischer | |
| 8,218,840 B2 | 7/2012 | Eisfeld et al. | |
| 2001/0053557 A1 | 12/2001 | Park | |
| 2002/0054291 A1 | 5/2002 | Tsai et al. | |
| 2003/0169916 A1 * | 9/2003 | Hayashi et al. | 382/145 |

(Continued)

OTHER PUBLICATIONS

Taiwanese Office Action for Taiwan Application No. 098130087, mailed Nov. 26, 2014, 4 pages.

*Primary Examiner* — Thomas A Hollweg
(74) *Attorney, Agent, or Firm* — Dicke, Billig & Czaja, PLLC

(57) ABSTRACT

Wafer edge inspection approaches are disclosed wherein an imaging device captures at least one image of an edge of a wafer. The at least one image can be analyzed in order to identify an edge bead removal line. An illumination system having a diffuser can further be used in capturing images.

4 Claims, 8 Drawing Sheets

(56) References Cited

U.S. PATENT DOCUMENTS

| | | |
|---|---|---|
| 2004/0002154 A1 | 1/2004 | Palsson |
| 2004/0113939 A1 | 6/2004 | Zacks et al. |
| 2005/0013474 A1* | 1/2005 | Sim ............................. 382/145 |
| 2005/0036671 A1* | 2/2005 | Watkins et al. .............. 382/145 |
| 2006/0109343 A1 | 5/2006 | Watanabe et al. |
| 2006/0167583 A1 | 7/2006 | Sundar |
| 2006/0251314 A1 | 11/2006 | Eisfeld et al. |
| 2007/0057164 A1* | 3/2007 | Vaughnn et al. ............. 250/216 |
| 2007/0237514 A1 | 10/2007 | Pillman et al. |
| 2007/0258085 A1* | 11/2007 | Robbins et al. ............ 356/237.4 |
| 2007/0269100 A1* | 11/2007 | Higashi et al. ................ 382/149 |
| 2008/0212084 A1 | 9/2008 | Watkins et al. |
| 2008/0232672 A1* | 9/2008 | Birkner et al. ................ 382/145 |
| 2009/0161094 A1 | 6/2009 | Watkins |
| 2009/0195786 A1* | 8/2009 | Gastaldo ....................... 356/477 |
| 2009/0196489 A1 | 8/2009 | Le |
| 2011/0054659 A1 | 3/2011 | Carlson et al. |
| 2011/0141267 A1* | 6/2011 | Lev et al. ........................ 348/87 |

* cited by examiner

WAFER EDGE INSPECTION ILLUMINATION SYSTEM

CROSS-REFERENCE TO RELATED APPLICATIONS

This application is a divisional application of U.S. patent application Ser. No. 13/062,852, filed May 31, 2011, and titled "Wafer Edge Inspection", now U.S. Pat. No. 8,426,223, issued Apr. 23, 2013 that claims priority to U.S. national stage application claiming priority under 35 U.S.C. §371 to International Application Serial No. PCT/US2009/056208, filed Sep. 8, 2009, which claims the benefit of U.S. Provisional Patent Application Ser. No. 61/095,207 filed on Sep. 8, 2008; the teachings of all of which are incorporated herein by reference.

BACKGROUND

1. Technical Field

The present invention relates to an inspection system that inspects an edge surface of a semiconductor wafer or like substrate such as a microelectronics substrate to identify defects.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics. Therefore, there is a need for faster, more advanced computers and electronics. To satisfy this need, quality and efficiency is required, whether it be on an assembly line, on test equipment in a lab, on the personal computer at one's desk, or in home electronics and toys.

Manufacturers of semiconductors have made vast improvements in end product quality, speed and performance as well as in manufacturing process quality, speed and performance. However, there continues to be demand for faster, more reliable and high performing semiconductors. To assist these demands, better inspection is necessary to increase yields. One area that has been generally ignored is the edge of the semiconductor wafer. It is believed that inspection of such edge area will lead to better information on defects, thereby enabling improved process control and improved wafer yields.

In the past when attempts to inspect the edge of a semiconductor wafer were made, it was generally performed manually with the naked eye of a human operator. As with all human inspection, repeatability, training, and capture rate are subject to flux. It has recently been discovered that edge inspection is important for detecting delamination of thin films, chipping and cracking of the wafer, resist removal metrology, and particle detection that all cause yield issues in a modern fab. Furthermore, the edge of the wafer is a leading indicator of process status, and by monitoring the edge of the wafer for changes in appearance, tighter process control can be implemented.

SUMMARY

Aspects of concepts presented herein relate to a wafer edge inspection. In one aspect, a wafer edge illumination system includes a diffuser forming a slot accepting a wafer edge. The diffuser radiates lambertion light onto the wafer edge. At least one light source is directed at the diffuser with substantially no stray light being emitted. A pair of baffles are positioned on either side of the diffuser to prevent stray light from contacting the diffuser and from escaping the diffuser.

In another aspect, a method for inspecting a wafer includes positioning a wafer with respect to at least one imaging device and capturing at least one image of at least a portion of a wafer edge. The image is analyzed to identify an edge bead removal line. A wafer processing step is modified based on the identification of the edge bead removal line. The image can be color and/or grayscale in various embodiments. Moreover, the portion of the wafer edge can be a top surface of the wafer and/or a surface normal to the top surface.

DETAILED DESCRIPTION

Currently, systems use only grey scale intensity to identify the location of Edge Bead Removal (EBR) lines. This works very well in most instances, but can suffer from a lack of resolution in some circumstances, leading to difficulties in determining the exact location or orientation of an EBR line. The use of color to enhance EBR line identification and tracking represents a significant improvement as many features present at the edge of a semiconductor wafer, often as a result of the size and/or nature of the materials themselves, present a strong palette of colors to an imaging system used in the inspection process.

One embodiment of the present invention separately analyzes each selected color channel, including grey scale, and combines the results of these analyses to obtain their results. As a matter of economy, the analysis of only a single color channel will be described herein.

One benefit of the present invention is that those images captured for the purpose of identifying and tracking EBR lines can be simultaneously used to identify defects at the edge of a wafer. Accordingly, some embodiments of the present invention will carry out multiple tasks, e.g. defect inspection, wafer metrology, and/or EBR inspection, simultaneously. Other embodiments may be primarily single purpose.

Figure 1:
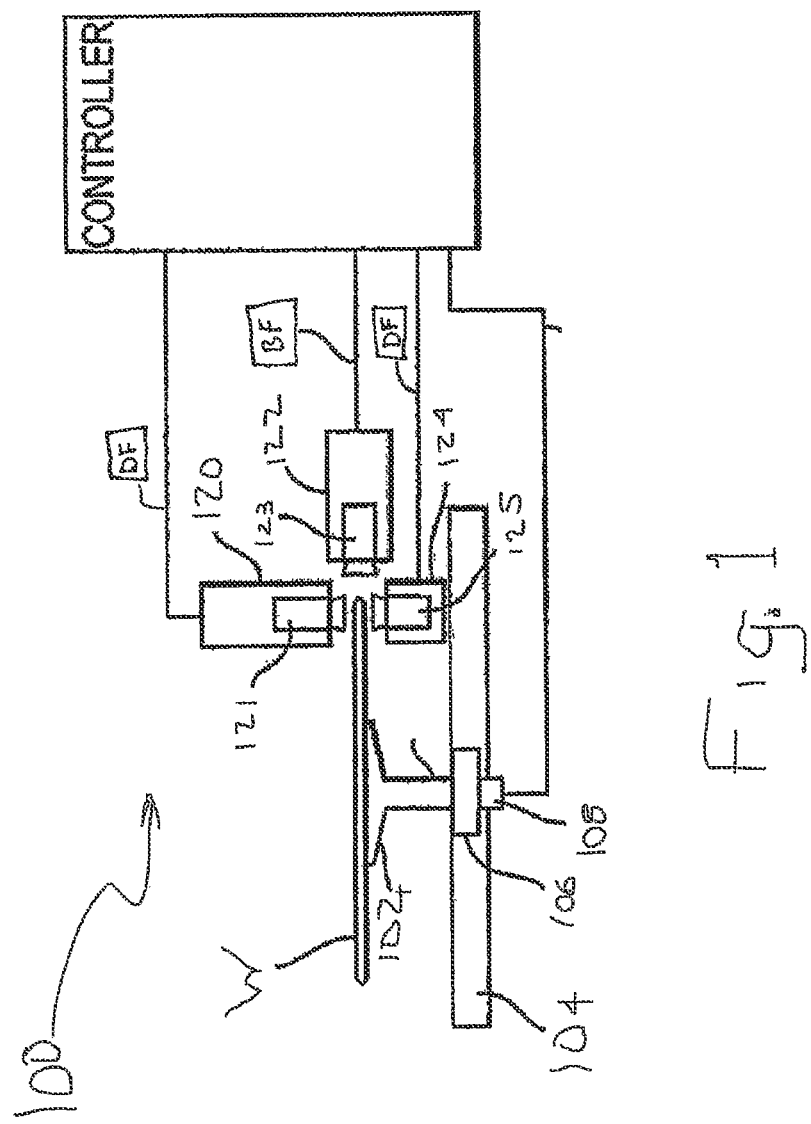
FIG. 1 is a schematic diagram of an edge inspection system.

A suitable optical system for use with the present invention is described in U.S. Pat. Nos. 6,947,588 and 7,366,344 to Sim, which patents are jointly owned herewith and are incorporated herein by reference in their entirety. FIG. 1 illustrates an embodiment of an inspection system 100 having a wafer support 102 mounted on a stage mechanism 104 that is adapted to laterally translate the wafer support 102 for alignment purposes. Wafer support 102 is rotated by motor 106 and the resulting rotation is monitored and reported to controller 110 by rotary encoder 108.

Images of the edge of a wafer W are captured by sensors 120, 122, and 124. Each of the sensors 120, 122, and 124 includes a camera 121, 123, and 125. Cameras 121, 123, and 125 include suitable optics and an imager such as a CCD or CMOS chip. Note that while system 100 illustrates three sensors 120, 122, and 124, fewer sensors may be included. For example, in one embodiment the invention consists only of sensors 120 and 124. In other embodiments, system 100 may include only sensors 120 and 122 or only sensor 122. Other combinations will be readily apparent to the skilled practitioner. Sensors 120, 122, and 124 are communicatively coupled to a controller 110 which controls the system 100 as more fully described below.

Figure 2:
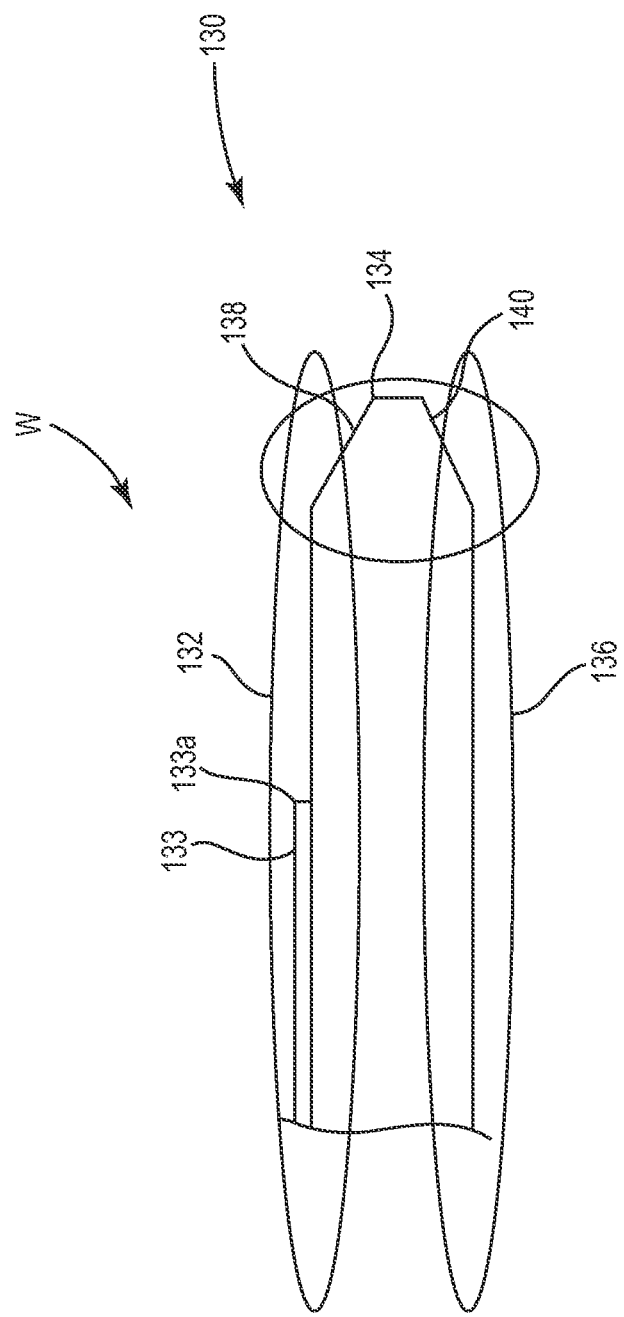
FIG. 2 is a schematic side view of a wafer edge.

With reference to FIG. 2, a wafer W has an edge 130 which, for convenience's sake, may be divided into a number of zones or regions. An edge top zone 132 which may include a resist layer 133 or other films or structures formed on the top surface of the wafer W, an edge normal zone 134, and an edge bottom zone 136. Note that the aforementioned zones or regions overlap one another at the upper and lower bevels 138, 140 of the wafer edge 130. For example, an image of the edge top zone 132 may include portions of resist layer 133 and portions of the upper bevel 138 of the wafer W. It should also be kept in mind that the chamfered geometry of the wafer edge 130 illustrated in FIG. 2 is only one type of wafer edge geometry. A profile of a wafer edge 130 may be chamfered as shown or may have one of a number of curvilinear shapes, including a bull nose profile or an elliptical profile. In any case, the zones described above are useful for discussing imaging and inspection issues relating to the edge 130 of a wafer W.

Resist layer 133 is representative of the layers and structures that form semiconductor devices on a wafer W. The sharp boundary 133a of layer 133 represents an edge exclusion boundary. In general it is not acceptable to form layer 133 beyond boundary 133a as the materials that form layer 133 will not generally stay reliably adhered to the wafer edge 130 in zone 132. Boundary 133a is formed by any of a number of masking, spin coating, etching (wet or dry), cleaning (wet or dry), or mechanical polishing techniques. Failures or variations in any of the aforementioned techniques, in the materials used, or in the conditions under which the process takes place may cause variations at the edge of a wafer that can lead to damage or degradation to the wafer W itself or, more often, to the devices formed thereon.

Figure 3:
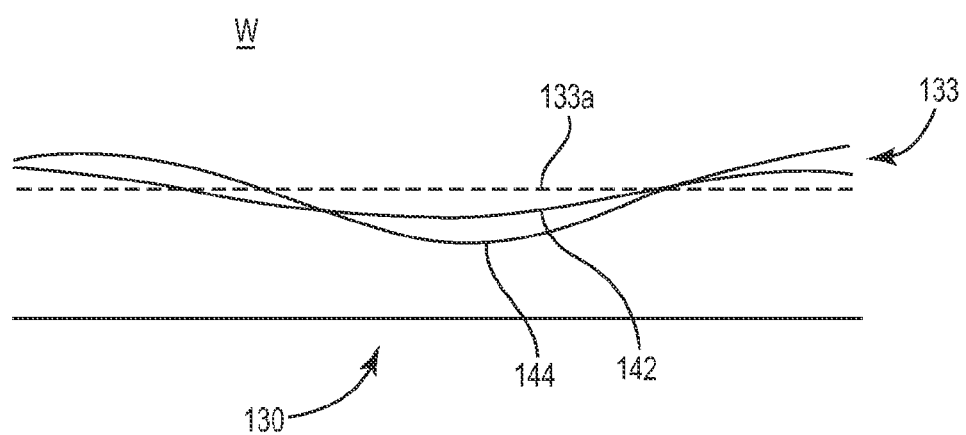
FIG. 3 is a schematic top view of a wafer edge.

FIG. 3 is a top schematic view of a portion of a wafer edge 130. Note that this schematic image is normalized such that the curvilinear edge of the wafer W appears to be straight. It is an ideal consideration for all layers 133 formed on a wafer W to end at boundary 133a, shown in its nominal position in dashed lines. In practice however, it is often the case that deposited materials such as photo resist and the like will be deposited in a much more variable manner. As multiple layers of resist can be formed on a single wafer W, issues related to this variability can arise. For example, where a first resist (or other material) layer 142 extends past boundary 133a, it becomes more likely that the portion that extends beyond the boundary 133a will break off, thereby contaminating the rest of the wafer W. A subsequent layer of resist (or another material) 144 that is intended to be adhered to layer 142 may also flake or chip away due to the likelihood of the underlying layer to flake or chip. Further, where an underlying layer, such as layer 142 is intended to fully cover the wafer W itself or a layer that lies beneath the underlying layer 142 but does not, the layer 144 deposited thereover may not adhere at all. For these and other reasons, it is undesirable for layers such as layers 133, 142, and 144 to extend beyond the nominal boundary 133a. Similarly, it is also undesirable for the edges of layers such as layers 133, 142 and 144 to cross one another.

In one embodiment, sensors 120, 122, and 124 are adapted to capture images of edge top zone 132, edge normal zone 134, and edge bottom zone 136, respectively. Further, sensors 120, 122 and 124 also capture images of the upper and lower bevels 138, 140 of the wafer edge 130. Sensor 120, being located above the wafer W and directed generally downward, may capture an image of resist layer 133. Sensor 120 may be arranged such that an optical axis thereof is substantially normal to the surface of the wafer W or inclined at an oblique angle. Sensor 124 essentially mirrors the arrangement of sensor 120 and may be arranged at a normal or oblique angle to the under-surface of the wafer W. Sensor 122 is generally placed such that an optical axis thereof is substantially in the plane of the wafer W. In one embodiment, the optical axis of sensor 122 is arranged normal to the edge 130 of the wafer W. In another embodiment, sensor 122 may be arranged at an oblique angle to the wafer edge 130. In both instances, the sensor 122 remains substantially in the plane of the wafer W so as to enable the sensor 122 to capture images of both the upper and lower bevels 138, 140 of the wafer edge 130. It is contemplated that the sensor 122 may also be arranged out of the plane of the wafer W, in either of a normal or oblique relationship to the wafer edge 130, so that the sensor 122 may capture more of the upper or lower bevels 138, 140 in a single image. In this embodiment, more than one sensor 122 may be provided so as to capture more of the upper and lower bevels 138, 140 simultaneously.

Figure 4:
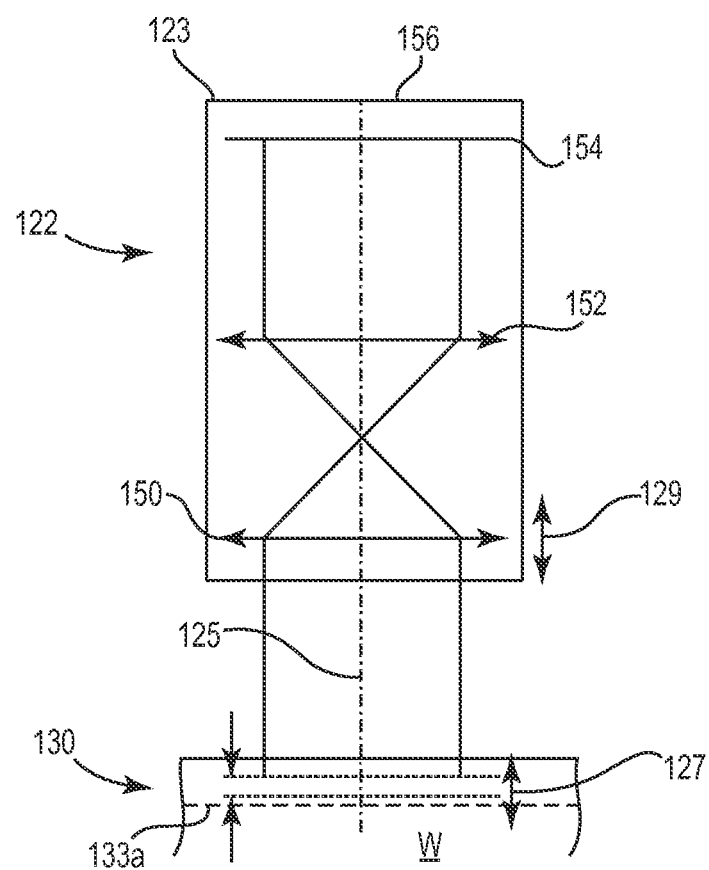
FIG. 4 is a schematic view of a sensor.

Sensors 120, 122 and 124 are, for the sake of brevity, assumed to be essentially the same; accordingly, only sensor 122 will be described in detail. Differences between the sensors 120, 122, and 124 will be noted where appropriate. FIG. 4 illustrates schematically a sensor suitable for use in the present invention. It is noted that the illustrated sensor is what is known as an area scan sensor in that it captures a two dimensional image. It is also possible to use a line scan sensor arrangement which is not shown.

Camera 123 of sensor 122 includes optics, in this embodiment consisting of lenses 150 and 152, and an imaging chip 154. These elements are generally located in a housing 156. Taken together, elements 150-156 form a camera. While only two lenses are illustrated, it will be appreciated that the number of lenses may be increased or decreased and that additional optical elements such as filters and polarizers may be included, depending on the application. Additional elements (not shown) such as electronics for capturing signals from the imaging chip 154 and transmitting them to a controller 110 are included in the housing 156.

The imaging chip 154 may be any suitable device including a CCD or CMOS chip that has the requisite pixel count, pitch, and frames per second (FPS). In one embodiment, the imaging chip 154 may be a CMOS Bayer chip having a native resolution of 1280×720 and a frame rate of >60 fps (frames per second). Another embodiment may use a grey scale only CCD imaging chip 154. Yet another embodiment may include a three chip color camera having three separate imaging chips 154 of CCD or CMOS configuration.

The optical elements of camera 123 define an optical axis 125. These optics also define a field of view, which is the area or size of an image that is captured by the camera, and a depth of field 127. The depth of field 127 is that portion of the object, in this case the edge 130 of wafer W that is in focus. Focus can be defined a number of ways, but for present purposes, "being in focus" will be defined as that a portion of an object (e.g. wafer W) visible in the field of view that has sufficient clarity or resolution for the purposes for which the image is captured, in this case inspection of the edge 130 of a semiconductor wafer W.

The depth of the depth of field 127 is defined by the optics used to capture an image and may be modified by modifying or replacing various portions of the optics of the camera 123. In one embodiment, the act of focusing the camera 123 at a particular location on the wafer edge 130 involves moving lens 150 along optical axis 125 as indicated by arrow 129. Those skilled in the art will recognize that other methods of moving the depth of field 127 along the optical axis exist and accordingly, the present discussion will be limited for brevity's sake.

Figure 5:
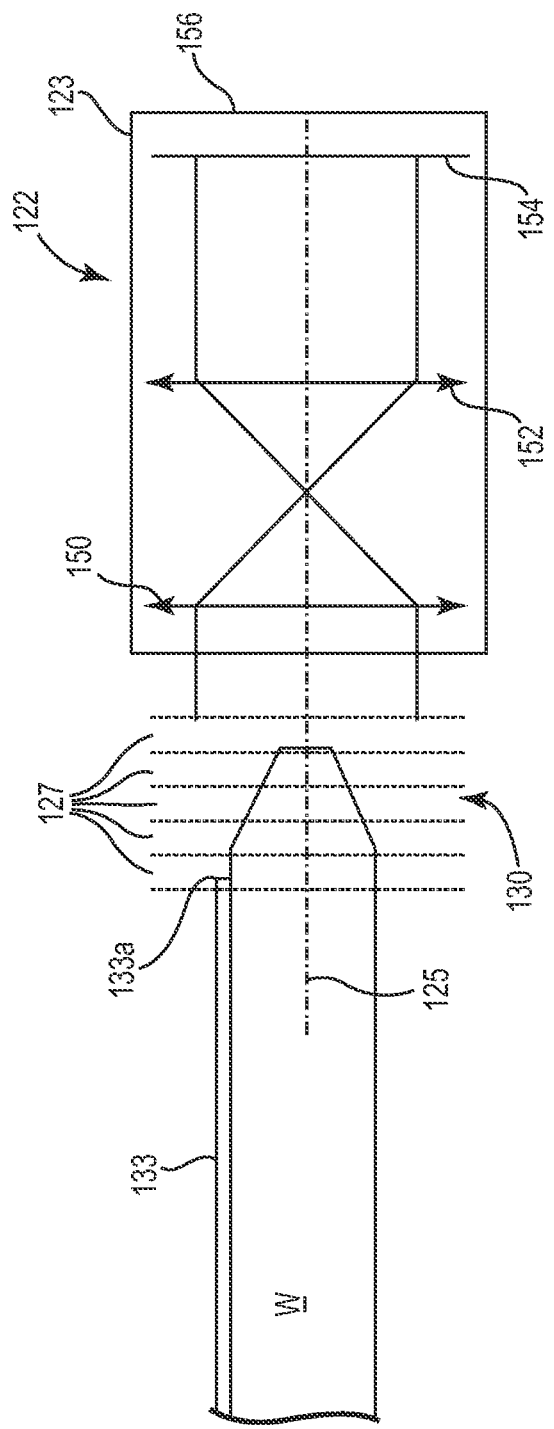
FIG. 5 is a schematic side view of a sensor and wafer edge illustrating variations in a depth of field.

As seen in FIG. 5, the depth of field 127 can be moved, step wise or continuously, across substantially the entire wafer edge 130, thereby capturing images of substantially the entire wafer edge 130, the images each having at least a portion of the wafer edge 130 in good focus. Taken together, the images include substantially all of the wafer edge 130 in good focus. Ideally, one could design an optical system for camera 123 having a large enough depth of field 127 such that the entire wafer edge 130 may be imaged in focus in a single instance. While such optics are possible, they are considered to be far too expensive.

Illuminating the edge 130 of a wafer W is a difficult proposition. Silicon, from which most wafers W are made, is highly reflective as are many of the materials applied to the wafers W during device fabrication. Other materials such as bottom antireflective coatings (BARC) absorb most light incident thereon. These variations, taken together with the complex geometry of the wafer edge 130, make a one-size-fits all approach to illumination problematic.

Different approaches to illumination are used to identify different types of defects or features on a wafer W. Brightfield illumination, involves directing light onto a surface being imaged in such a manner that the light, upon specular reflection, will be directed into or collected by the imager. Under brightfield illumination conditions, contrast in an image is obtained through the scattering of incident light onto optical paths that are not collected by an imager. Accordingly, the object being imaged appears bright and defects or discontinuities that scatter light appear dark, i.e. dark against a bright field. Darkfield illumination involves directing light onto a surface being imaged in such a manner that the light, upon specular reflection, will be directed away from an imager. Under darkfield illumination, contrast is obtained by the scattering of incident light onto optical paths that are collected by an imager. In this setting, the object being imaged appears dark and defects, particles and other discontinuities that scatter light appear bright, i.e. bright on a dark field.

In general, brightfield illumination is useful in illuminating features and variations within the otherwise specularly reflective wafer W that have generally smooth surfaces, e.g. layer boundaries, color variations and the like. Darkfield illumination is useful in illuminating features, particles and variations in or on the wafer W that are discontinuous or which have features that would tend to scatter light. It will be appreciated then, that when one desires to inspection a wafer edge 130 for the existence of chips, cracks, particles, EBR lines, and process variations, it is desirable to utilize a combination of brightfield and darkfield illumination.

Figure 6:
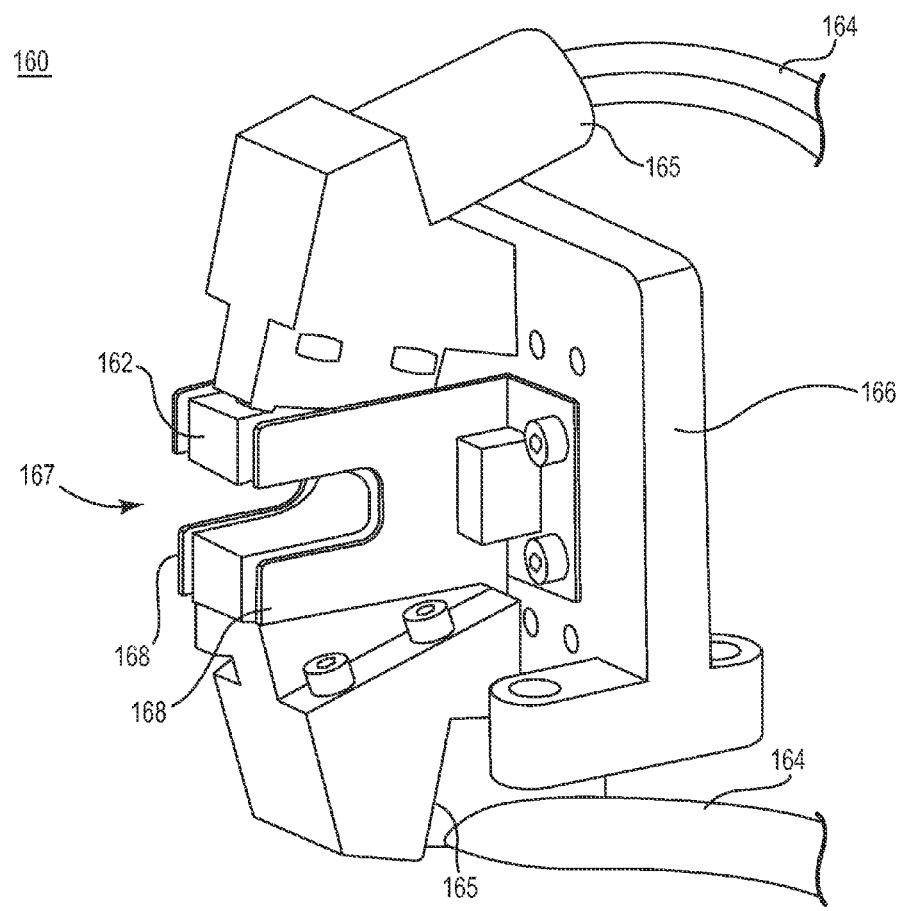
FIG. 6 is an isometric view of an illumination system.
Figure 7:
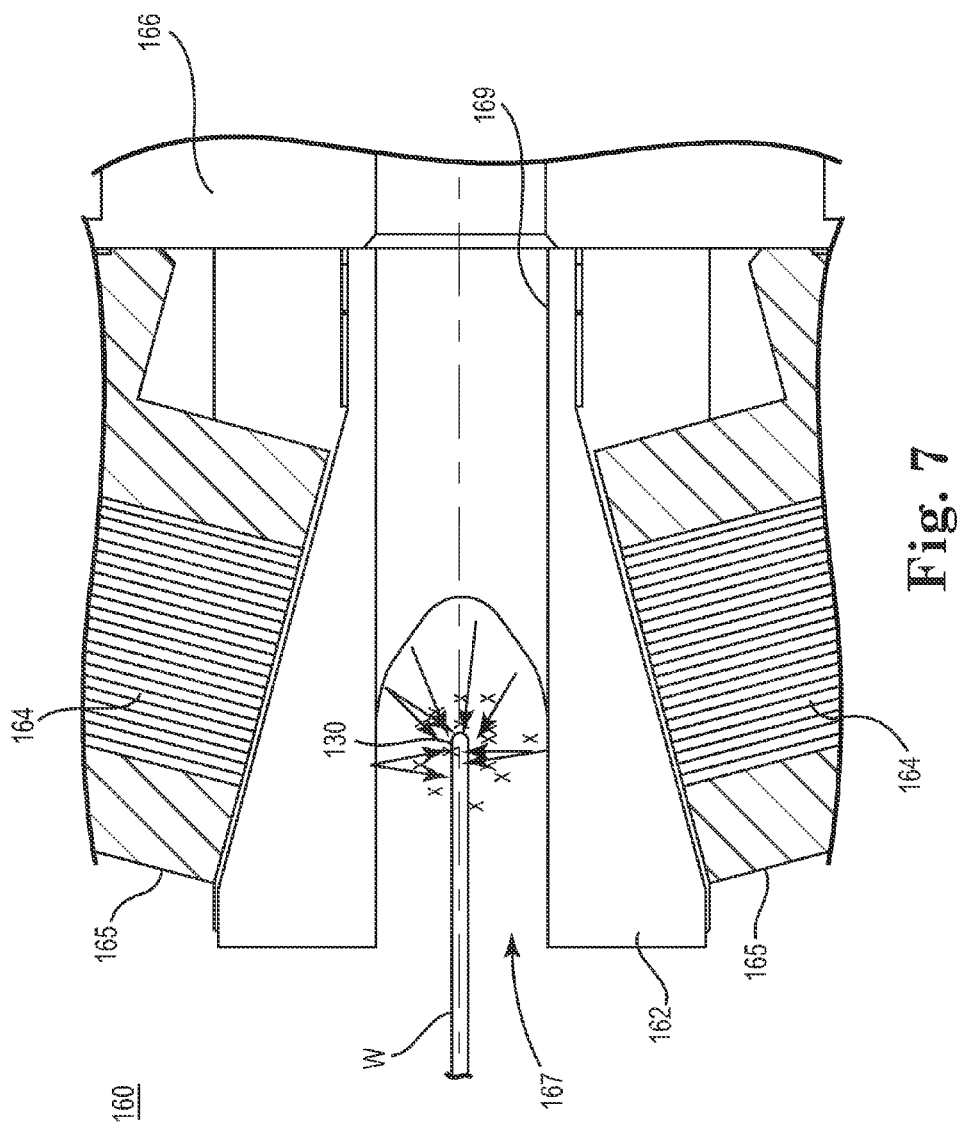
FIG. 7 is a schematic sectional view of an illumination system illuminating a wafer edge.

FIGS. 6 and 7 illustrate one embodiment of an illumination system 160 for a sensor 122 intended primarily for illuminating region 134 of wafer edge 130, including wafer bevels 138 and 140, though as will be described hereinbelow, the diffuse nature of this illuminator provides sufficient illumination to regions 132 and 136 for imaging portions of those regions as well. Illumination system 160 includes a diffuser 162 that receives illumination from one or more optical fiber/conduit sources 164. Diffuser 162 is mounted on a bracket 166 such that an aperture 167 is positioned around wafer edge 130 as illustrated in FIG. 7. Baffles 168 isolate diffuser 162 from illumination from sources other than fiber sources 164. The diffuse light from diffuser 162 is incident on the wafer edge 130 to provide what is essentially brightfield illumination of the wafer edge 130, though it should be understood that the diffuse nature of the incident light means that some portion of the illumination is incident on the wafer edge 130 in a darkfield manner with respect to a sensor 120, 122 or 124.

Illumination sources 164 transmit light using low loss optical conduits or fiber directly to the diffuser 162 from a suitable light source coupled thereto. In one embodiment, optical fibers (not shown) of source 164 are placed directly in contact with the diffuser 162 by lugs 165 which are themselves coupled to the bracket 166. In other embodiments, the sources 164 are positioned immediately adjacent to the diffuser 162 so as to direct substantially all of the light provided by the sources 164 into the diffuser and minimize the amount of stray light introduced into the environment of sensor 122.

Baffles 168 prevent the incidence of light from darkfield illumination sources onto the diffuser 162, thereby providing a user of a system to cleanly separate brightfield and darkfield illumination channels. Note that though darkfield illumination was defined above, illuminators that provide substantially only darkfield illumination are not illustrated for the sake of brevity only. Those skilled in the art will readily appreciate that darkfield illumination can be at any angle and azimuth of incidence upon the wafer W so long as the incident light is not specularly reflected into the sensor being used to image the wafer W. Baffles 168 are particularly useful where a sensor 120 or 124 is used to image regions 132 or 136, respectively, using darkfield illumination (see e.g., DF on FIG. 1, indicating a darkfield illumination source coupled to sensor 120 and/or 124) while sensor 122 is used to simultaneously image wafer edge 130 using brightfield illumination see e.g., BF on FIG. 1 indicating a brightfield illumination source coupled to sensor 122) from diffuser 162. Where the field of view of sensors 120 and 124 are sufficiently close to that of sensor 122, the likelihood of stray light is increased and baffles 168 act to cut down such light. In some embodiments, darkfield illumination in the form of a laser or high intensity broadband source (not shown) is directed onto wafer edge 130 within the field of view of the sensor 122. In this embodiment, both bright field and darkfield illumination are possible simultaneously and the baffles 168 prevents the darkfield illumination from being incident on the diffuser 162.

FIG. 7 is a cross-section illustration of illumination system 160 from the side. Edge 130 of wafer W is received in aperture 167. Light provided to diffuser 162 by fiber sources 164 is re-emitted by diffuser 162 and is incident upon wafer edge 130 in a diffuse, Lambertian fashion. The diffuse nature of the light incident upon wafer edge 130 results in illumination of the wafer edge 130 that is both brightfield and darkfield in nature, though brightfield type illumination predominates. In one embodiment, images of the wafer edge 130 are captured by sensor 122 through a bore 169 through the otherwise solid diffuser 162 which is radially oriented to the wafer W. In another embodiment, diffuser 162 is solid and sensor 122 is directed at wafer edge 130 at an angle to the radial direction of the wafer W or as described in US patent application no. 20070057164, which is jointly owned herewith and hereby incorporated by reference, with illumination system 160 being oriented so as to illuminate the field of view of sensor 122 (and/or sensors 120, 124).

While illumination provided by fiber sources 164 is somewhat attenuated by the diffuser 162, the fiber sources 164 are able to provide high levels of illumination that provide more than enough illumination for sensor 122 to capture images of the wafer edge 130. The efficiency of the illumination through diffuser 162 is such that illumination of light absorbing substrates or light absorbing materials on otherwise diffuse or specular substrates is possible without creating large amounts of stray light that negatively affect image quality of images captured by sensor 122. Further, the use of sources 164 allows light sources (not shown) such as arc lamps, lasers, bulbs or other sources to be positioned remotely from the location at which the wafer W is imaged to simplify system design and packaging. In some embodiments the illumination provided through sources 164 to diffuser 162 is monochromatic. In other embodiments the light is polychromatic in nature. Further, multiple sources each providing one or more wavelength or wavelengths may be provided to introduce light into sources 164.

As can be seen in FIG. 5 the depth of field of sensor 122 (or sensors 120 or 124) may not encompass the entire wafer edge 130. However, using image fusion techniques, multiple substantially registered (aligned) images of a selected part of the wafer W can be concatenated to provide a composite image having high resolution and wherein substantially the entire portion of the wafer edge 130 contained in the image is in proper focus. The concatenation process selects those portions of each of a set of registered images that is substantially in focus and places them in the resulting composite image.

Figure 8:
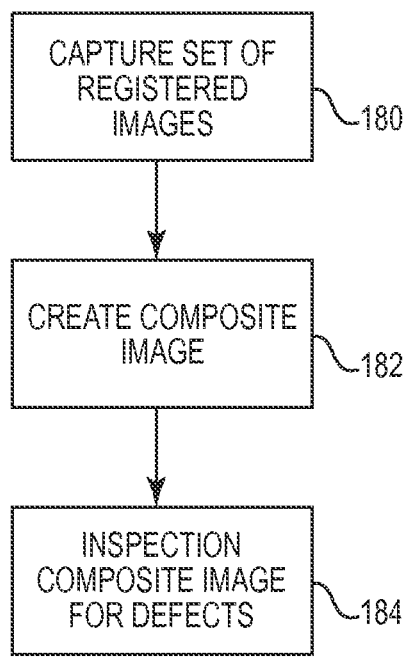
FIG. 8 is a flow diagram of a method for edge inspection.

As seen in FIG. 8, an edge inspection system 100 facilitates the formation of composite images of the wafer edge 130 by capturing images of the wafer edge 130 while moving the depth of field 127 inwardly or outwardly as needed in a stepwise or continuous fashion. The wafer 130 may be rotated, stepwise to sequentially present substantially the entire periphery of the wafer W. Each portion of the periphery may be scanned in a stop-and-shoot type of arrangement or the wafer may be continuously rotated and illumination system 160 may be operated in a strobe illumination schema to freeze the motion of the wafer as it rotates, one image of each set of registered images being captured on each rotation. In this manner, substantially the entire wafer edge 130 is imaged in the proper focus, though the various properly focused portions are distributed amongst the set of registered images. (Step 180)

Multiple image processing techniques exist for mathematically identifying those portions of an image that are in focus and concatenating or combining the focused portions to form a composite image. Some of these techniques may include linear superposition, nonlinear methods, optimization approaches, artificial neural networks, image pyramids, wavelet transform, and generic multi-resolution fusion schemes. (Step 182)

Once composite images of the periphery of a wafer are formed, those images may be inspected as described in US patent application no. 20080013822 to Pai et al, which application is jointly owned with the present application and hereby incorporated by reference, or the composite image may be inspected as described in U.S. Pat. Nos. 6,947,588 or 7,366,344 to Sim, which patents are jointly owned herewith and hereby incorporated by reference. (Step 184) Note that the multiple composite images obtained at step 182 may be further compressed in step 184 during the inspection process as described in the aforementioned patent application and patents.

As described in US patent application no. 20080013822 to Pai et al, which is jointly owned herewith and hereby incorporated by reference, finding and analyzing EBR lines at the edge 130 of a wafer W is an important task. In addition to discriminating EBR lines based on grayscale intensity, it is desirable to perform EBR line analysis and inspection using color as a discriminator. In one embodiment, images are deconstructed to identify RGB, HSV, HSL, HIS or HSB (color measurement scales) values for each pixel in an image.

In addition to the analysis and inspection of EBR lines using images captured using an edge top sensor 120 as described in the aforementioned application no. 20080013822, it is also possible to analyze EBR lines using images captured from edge normal sensor 122. As will be appreciated, it is not necessary to normalize the edge normal images to account for the possibility that the wafer is off center on its support 102, however it is necessary to account for the fact that the periphery of a wafer is not likely to be perfectly flat and that as a result, the edge normal image of the wafer edge 130 will "move" vertically around the periphery. However, because the top and bottom surfaces of the wafer W provide good references with relatively high contrast, it is a simple matter to identify the upper and lower surfaces of the wafer W in an edge normal image using a simple thresholding routine as it is generally the case that because there is nothing to reflect or scatter light above or below a wafer W in an edge normal image, pixels located above or below the image of the wafer edge 130 tend to be very dark and accordingly, the relatively lighter wafer W can be distinguished. Adjacent images may be vertically adjusted with respect to one another before or after the image compression referenced in the aforementioned application no. 20080013822. Once this vertical normalization is complete, grayscale or color values are used to identify EBR lines on the edge 130 of the wafer.

One reason color pixel characteristics have been found to be useful is that on the edge 130 of a wafer, the significant curvature of the wafer's edge is such that there may be significant linear features that are a function of the shape of the wafer and/or the illumination or optics of the system 100. Conversely, most EBR lines exhibit useful color signatures that allow EBR lines to be distinguished from geometric features of the wafer W itself. For example, in some embodiments an EBR line will be formed by a layer of some material laid down on the wafer W that has a characteristic color. Because there is a sharp color-based gradient at the boundary between two differently colored materials, greater resolution of the EBR lines can be had.

In another embodiment, multiple analyses of the EBR lines may be made on grayscale, RGB, HSV, HSL, HIS or HSB bases and then compared to distinguish between native geometry of the wafer and EBR lines present on the edge of a wafer. In this way edges that may be indeterminate in one color regime may be identified using other color regime. For example, channels of color regimes may be cross referenced or otherwise correlated with one another to provide additional resolution information.

Conducting EBR analysis on edge normal lines is itself useful alone or in conjunction with edge top EBR analysis as edge normal images can provide information about whether an EBR line extends below the apex of the wafer edge 130. Note that EBR lines can be formed by actual layers of material or by the absence of layers of material such as where an etchant or other chemical changed the existing structure of the wafer W. In this respect, edge normal images can provide additional information as to the source of contamination, cracks, chips or other problems with a wafer W.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

We claim:

1. A wafer edge illumination system comprising:
a diffuser having a slot formed therein for accepting a wafer edge, the diffuser being adapted to radiate lambertian light onto the wafer edge;
at least one light source directed directly into the diffuser with substantially no stray light being emitted and such that light emitted by the diffuser is incident upon the wafer edge in a diffuse, lambertian fashion;
a pair of parallel light baffles, each of the pair having a slot formed therein for accepting the wafer edge and each positioned to either side of the diffuser to prevent stray light from contacting the diffuser and to prevent stray light from escaping the diffuser such that the diffuser is a high efficiency light source for illuminating the edge of the wafer.

2. The illumination system of claim 1 wherein the at least one light source is a brightfield illumination source and wherein the system further includes a darkfield illumination source for illuminating a field of view of the wafer edge simultaneous with the illumination of the wafer edge by the diffuser from the brightfield illumination source the baffles acting to separate the illumination sources.

3. The illumination system of claim 2 wherein the brightfield illumination source and the darkfield illumination source are of different wavelengths.

4. The illumination system of claim 3 wherein there exists substantially no optical coupling between the brightfield illumination source and the darkfield illumination source.

* * * * *

UNITED STATES PATENT AND TRADEMARK OFFICE
CERTIFICATE OF CORRECTION

PATENT NO. : 9,062,859 B2  
APPLICATION NO. : 13/868710  
DATED : June 23, 2015  
INVENTOR(S) : Christopher Voges et al.

Page 1 of 1

It is certified that error appears in the above-identified patent and that said Letters Patent is hereby corrected as shown below:

Specification

Column 2, line 1, delete "lambertion" and insert in place thereof --lambertian--.

Column 6, line 36, delete "see" and insert in place thereof --(see--.

Signed and Sealed this
Ninth Day of February, 2016

Michelle K. Lee
*Director of the United States Patent and Trademark Office*